United States Patent [19]

Fielding

[11] 4,154,753

[45] May 15, 1979

[54] FLUORINATED COMPOUNDS CONTAINING FUNCTIONAL GROUPS

[75] Inventor: Harold C. Fielding, Runcorn, England

[73] Assignee: Imperial Chemical Industries Limited, London, England

[21] Appl. No.: 215,222

[22] Filed: Jan. 3, 1972

Related U.S. Application Data

[60] Continuation-in-part of Ser. No. 870,250, Sep. 4, 1969, abandoned, which is a division of Ser. No. 604,132, Dec. 23, 1966, abandoned.

[30] Foreign Application Priority Data

Jan. 12, 1966 [GB] United Kingdom ................ 1425/76

[51] Int. Cl.$^2$ .................... C07C 43/12; C07C 143/00
[52] U.S. Cl. ............................... 260/456 F; 546/312; 546/236; 260/567.6 F; 260/969; 260/502.4 R; 260/343.6; 260/327 R; 260/501.21; 260/459 R; 260/543 R; 260/512 R; 260/544 R; 260/559 R; 260/513 R; 260/584 R; 260/575; 260/573; 260/457; 260/453 AR; 260/562 A; 260/556 AR; 260/455 R; 560/221; 560/104; 560/192; 568/615; 568/677; 568/649; 568/655

[58] Field of Search ........... 260/459 R, 456 F, 612 D, 260/613 R, 615 R, 615 B, 501.21, 293.83, 327 R, 343.6, 502.4, 969, 567.6, 543 R, 512 R, 544 R, 559, 513 R, 584 R, 575, 573, 457, 453, 558, 456 F, 614 F, 613 D; 560/221, 104, 192

[56] References Cited

U.S. PATENT DOCUMENTS

| 2,982,786 | 5/1961 | McCane ........................ 260/614 F X |
| 3,159,609 | 12/1964 | Harris et al. .................. 260/614 F X |
| 3,277,068 | 10/1966 | Wall et al. ..................... 260/612 D X |
| 3,655,765 | 4/1972 | Gelfand ......................... 260/614 F X |

FOREIGN PATENT DOCUMENTS

1130822  10/1968  United Kingdom .................... 260/612

OTHER PUBLICATIONS

Shepard et al., Jour. Org. Chem., vol. 23, (1958), 2011–2012.

*Primary Examiner*—Bernard Helfin
*Attorney, Agent, or Firm*—Cushman, Darby & Cushman

[57] ABSTRACT

Surface-active products containing a highly fluorinated aliphatic substituent are prepared by nucleophilic attack of an oligomer of tetrafluoroethylene with an organic hydroxy compound in association with a proton acceptor.

1 Claim, No Drawings

FLUORINATED COMPOUNDS CONTAINING FUNCTIONAL GROUPS

This application is a continuation-in-part of U.S. Application Ser. No. 870,250, now abandoned, filed Sept. 4, 1969, which is an application divided from U.S. Application Ser. No. 604,132 filed on Dec. 23, 1966, now abandoned.

This invention relates to highly fluorinated compounds, particularly to ethers derived from unsaturated oligomers of tetrafluoroethylene.

U.K. Patent Application No. 14992/65 (to which U.S. Application Ser. No. 537,689, now abandoned corresponds and of which the disclosure is incorporated herein by reference) describes novel, branched-chain, internally unsaturated perfluoroolefins and a process for making them comprising reacting tetrafluoroethylene with an ionic catalyst, for example potassium fluoride, in an inert organic solvent. These perfluoroolefins (which we describe as tetrafluoroethylene oligomers) have the empirical formula $(C_2F_4)_n$ where n is at least equal to three and may be used for making highly fluorinated compounds possessing useful properties as surface-active agents.

We have now discovered that the perfluoroolefins are, surprisingly, susceptible to nucleophilic attack by oxy-anions derived from organic hydroxy compounds with the formation of ether derivatives of the perfluoroolefins and that this nucleophilic attack occurs mainly by the removal of fluoride from the oligomers and that very little or no addition takes place across the double bond of the perfluoroolefins. The oxyanions may be derived from the organic hydroxy compounds in conventional manner by using the hydroxy compound in conjunction with a proton acceptor. An alkali-metal derivative of an alcoholic or phenolic compound, derived by preliminary interaction of a hydroxy compound with a proton acceptor (e.g. a caustic alkali or an alkali-metal) may be used very conveniently as a source of the oxy-anions as nucleophiles.

The resulting products thus contain a highly fluorinated hydrocarbon group, derived from the oligomer molecule by loss of fluorine, and accordingly, possess the properties of low surface free energy which are well-known in the art to be inherently associated with highly fluorinated hydrocarbon groups. These properties render the products useful as surface-active agents of various kinds.

Thus our present discovery enables the known low surface free energy properties of highly fluorinated hydrocarbon groups to be utilised in surface-active agents by providing a method of attaching a highly fluorinated hydrocarbon group to another organic group.

Thus, according to our invention, we provide a process for the preparation of surface-active products containing a highly fluorinated substituent, which comprises subjecting an oligomer of tetrafluoroethylene (formula $(C_2F_4)_n$ where n is an integer at least equal to three) to nucleophilic attack, by an organic hydroxy compound in association with a proton acceptor.

The invention also provides novel products having the empirical formula $R_f(OR)_x$ wherein $R_f$ represents the residue of the oligomer after the removal of x fluorine atoms therefrom and OR represents the residue of an organic hydroxy compound after the removal of hydrogen from the hydroxyl group.

The products, which are all ethers, possess surface-active properties by virtue of the presence of the highly fluorinated substituent and the organic ether substituent in the same molecule. Because of the well-known low surface free energy properties of the highly fluorinated group, the fluorinated group and organic group have different affinities for given media. Thus the products of the invention are amphipathic, that is, one part of their molecules has an affinity for a particular medium, while another part of the molecules is antipathetic to the medium, and tend to be expelled from it, thus giving rise to the surface-active properties.

The term "surface-active" is used in the strict scientific sense and, inaccordance with the definition of Moilliet and Collie, *Surface Activity*, Van Nostrand Co., New York (1951), refers to a material which alters the conditions prevailing at interfaces, the surface-activity being due to the tendency of the material to be absorbed or deposited at the interfaces between liquids and external gaseous, liquid, or solid phases. The term "surface-active" is not restricted to one particular application of the surface-active properties, since as is well-known, any one surface-active material may be employed in a wide variety of particular compositions for specific applications, even though each of the compositions and applications takes advantage of the same surface-active property. For example, the fundamental interfacial process referred to as "wetting" can be utilised in an extremely large number of technical applications of a particular surface-active agent, for example in the removal of air from textiles, the displacement of air from powdered solids, in increasing the efficiency of contact pesticides, laying dust on roads and improving dust removal in filters, etc. In the like vein, a single surface-active agent may be useful as a detergent, an emulsifier, a bactericide, an anti-static agent, an ore-flotation agent or a foaming agent, etc. For example, the condensate product of ethylene oxide/propylene oxide and propylene glycol is a surface-active agent which has diverse commercial uses as an antistatic agent, a deduster, a defoamer, a demulsifier, a detergent, a dispersant, an emulsifier, a wetting agent, a foam controller and a dye bleacher. Accordingly, surface-active properties may encompass not only the phenomena occurring at liquid surfaces, but also phenomena occurring at solid surfaces (for example the reduction of friction at solid surfaces and increasing repellancy of surfaces to oils, water or other liquids.

Accordingly, the derivatives of the invention have the utility of having surface-active properties, in the broadest sense described above, by reason of the characteristic surface energy properties of branched perfluorocarbon groups. They may thus be used in many technical ways, for example the uses noted above as is common in the art with surface-active agents. However, as is also common in the art, the surface-activity properties imparted to the molecule by the fluorocarbon group, can be more efficiently used for certain technical applications when the derivatives contain certain functional groups.

Therefore, for many applications, it is desirable that the aromatic or aliphatic (including alicyclic) groups in the derivative contain groups having particular affinities or reactivities, for example hydrophilic groups, hydrophobic groups and polymerisable groups. The presence of such groups does not change the basic utility of the derivatives, but only increases efficiency of the derivatives for specific technical applications, as is common in the art.

The particular surface activity, and hence the specific technical application for which a derivative in accordance with the invention is most suitable, will thus depend upon the nature of the organic group in the derivative, for example, on whether the organic group is hydrophilic or oleophilic, whether it is polymerisable and whether it is cationic, anionic, n ionic or amphoteric. The properties of the compound depend upon the nature of the organic group and thus the selection of a derivative in accordance with the invention for a specific technical purpose may be made on principles well-known to those skilled in the art. For example, products in which the organic ether group contains an anionic group, for example when the organic group is a carboxylate salt, are especially useful in increasing the wetting effect of solvents; thus when the anionic group is hydrophilic, the derivatives are especially useful in aqueous systems as wetting, emulsifying and foaming agents. Similarly, products in which the organic groups are non-ionic, for example alkylene oxide adducts, have applications similar to those of anionic surfactants since their properties depend largely on the hydrophilic nature of the alkylene oxide group and thus are useful as emulsifying and spreading agents. The compounds in which the organic ether group contains a cation>active group, for example quaternary ammonium salts, absorb strongly on negatively charged interfaces and are useful in applications where a high degree of adhesion is required. The principles governing the selection of particular products in accordance with the invention for specific purposes are analogous to the principles used in selecting hydrocarbon surfactants for specific purposes.

In the process of our invention, the nucleophilic attack of an anion derived from the organic hydroxy compound may be achieved by using the organic hydroxy compound in conjunction with a proton acceptor. The optimum proton acceptor and the optimum conditions for carrying out the reaction depend to some extent upon the particular hydroxy compound employed. In general, the proton acceptor may be any base, but is preferably one which does not undergo undue reaction directly with the oligomer (i.e. without the participation of the hydroxy compound) under the conditions employed for the reaction. The proton acceptor and the conditions of reaction should be selected so as to produce, from the hydroxy compound, the oxy-anions required to serve as the nucleophilic reactant required.

Suitable proton acceptors include inorganic bases, for example alkali metal hydroxides and hydrides, and organic bases, for example tertiary amines. According to the nature of the organic hydroxy compound, it may be practicable to interact the hydroxy compound with the base to form a product which can then be used to react nucleophilically upon the oligomer. The more acidic the hydroxy compound the more readily this can be done; phenolic hydroxy compounds (i.e. compounds in which the —OH group is attached to a carbon atom of an aromatic ring system) can thus be reacted with an alkali metal hydroxide (more particularly sodium hydroxide or potassium hydroxide) to form a phenate, while aliphatic hydroxy compounds usually do not react as readily with alkali metal hydroxides and the alkali metal itself may be used as a more powerful proton acceptor to bring about formation of the desired alkali metal derivative. Accordingly, this intermediate formation of the alkali metal derivative as an intermediate product for carrying out the process of our invention is an especially convenient procedure but it is not essential for the successful operation of our process. For the less acidic hydroxy compounds, one can convert these into metal derivatives by reaction with a more powerful proton acceptor (e.g. alkali metal or alkali metal hydroxide) or simply use them in conjunction with the proton acceptor and especially in conjunction with an organic amine.

When an amine is used, it may be an amine having an aliphatic, aromatic or heterocyclic group attached to the basic nitrogen atom or an amine in which the basic nitrogen atom is contained in a cyclic system. The groups or atoms attached to the basic nitrogen atom may be the same or different. The preferred amines are tertiary amines containing at least two lower alkyl groups (i.e. alkyl groups containing one to six carbon atoms such as methyl, ethyl, propyl, hexyl and any isomeric forms thereof) attached to the basic nitrogen atom, for example aryl dialkyl amines, cycloalkyl dialkyl amines and trialkyl amines optionally containing one longer alkyl group, for example an octyl, decyl or octadecyl group. Examples of such amines include:

N,N-dimethyl aniline,
N,N-diethyl aniline,
N,N-dimethyl cyclohexyl amine,
N,N-dimethyl secondary octyl amine.

The amines especially preferred are tr-n-alkyl amines, for example trimethylamines, dimethylethylamine, diethylbutylamine, tributylamine; the amine usually found most useful is triethylamine.

Examples of heterocyclic amines which may be used are N-methylpiperidine, N-methylpyrrolidine, and N-methylmorpholine; of these N-methyl piperidine usually gives the best results.

The reaction is generally conducted in an inert anhydrous solvent medium. While the particular solvent is not critical, preferred solvents include aliphatic and aromatic sulphoxides, ethers, hydrocarbons, esters, carboxylic amides, phosphoramides, alcohols, halocarbons and nitriles, for example dimethyl sulphamide, benzene, toluene, xylene, trichlorotrifluoroethane, dimethylformamide, dimethylacetamide, acetonitrile, propionitrile, acetone, diethyl ether, the dimethyl ether of ethylene glycol, and the dimethyl ether of diethylene glycol, ethanol, dioxane, dimethoxydiethylene glycol, tetrahydrofuran and hexamethylphosphoramide. Dimethylformamide and toluene are especially preferred solvents. Mixtures of solvents may be used if desired.

The particular organic hydroxy compound used as a starting material will clearly be governed by the particular oligomer derivative required and, of course, in some cases it may be conveninet to modify the organic group after the reaction with the fluorocarbon oligomer, for example an aromatic group in a first-formed oligomer derivative may subsequently be substituted to give a required derivative.

The organic hydroxy compound may contain one or more hydroxy groups, and when a plurality of hydroxy groups is present more than one of these may react with oligomer molecules so forming products of the type $R(OR_f)_x$. Similarly more than one fluorine atom of the oligomer may react, so giving rise to products of the type $(RO)_xR_f$.

The organic hydroxy compound may optionally contain one or more aromatic groups and, in this case, the hydroxy group (or groups) may be attached either directly or indirectly to an aromatic nucleus. Compounds containing aromatic groups are especially useful since, as noted above, the oligomer derivatives obtained with them may readily be modified by substitution in an aromatic group in conventional manner.

Among the range of organic hydroxy compounds containing aromatic groups which may be used in the invention are compounds containing a single aromatic nucleus, for example benzene derivatives, and compounds containing condensed aromatic nuclei, for example derivatives of naphthalene and anthracene. If desired, the aromatic group may be a heterocyclic group, for example pyridine. The hydroxy group (or groups) is preferably attached directly to a carbon atom of the aromatic nucleus so that the oligomer group becomes attached to an oxygen atom directly bonded to an aromatic nucleus. Preferred aromatic hydroxy compounds are those which contain six-membered aromatic rings, especially compounds having a benzene or naphthalene nucleus, for example phenol, the o-, m- and p-cresols, catechol, resorcinol and the alpha and beta naphthols. When the aromatic compound contains two or more hydroxy groups, a separate perfluorocarbon residue may become attached to the oxygen atom of each of these groups. Hence, in this form of the invention, compounds of the general formula $Ar(OR_f)_x$ are produced where x is an integer, preferably equal to one or two, $R_f$ is the residue of the perfluoroolefin oligomer which will have the formula $C_{2n}F_{4n-1}$ and Ar is the aromatic nucleus.

The aromatic nucleus may be substituted with other groups in addition to the aforesaid hydroxyl groups, for example with one or a multiplicity of the groups alkyl, aralkyl, aryl, alkoxyl, aryloxy, nitro, halo, carboxyl ester, and sulphonyl ester. In each of the foregoing the alkyl is preferably lower alkyl containing, for example, up to four carbon atoms. Of course, the substituent groups which may be present in addition to the aforesaid hydroxyl should be inert towards the oligomer and the other components of the reaction system. In general, the reaction may conveniently be carried out at temperatures up to about 150° C., the preferred temperature depending upon the nature of the hydroxy compound.

For convenience, compounds containing hydroxy groups directly bonded to aromatic rings (which may be condensed or heterocyclic rings) will be referred to as phenolic hydroxy compounds and the hydroxy groups directly bonded to the aromatic rings will be referred to as phenolic hydroxy groups. Compounds containing hydroxy groups not bound directly to an aromatic ring will, for convenience, be referred to as alcoholic hydroxy compounds and the hydrogen groups will be referred to as alcoholic groups. It is to be understood, however, that the alcoholic hydroxy compounds as defined above may be purely aliphatic or may contain aromatic groups.

When a phenolic hydroxy compound is used, the reaction is preferably carried out at temperatures from room temperature upwards to 150° C. At the higher temperatures in that range, for example 70° C. to 150° C., there is a tendency for the oligomer to be attacked by more than one molecule of the phenolic compound to form compounds have the general formula $R_f(OAr)_2$ where $R_f$ is a residue of a tetrafluoroethylene oligomer wherein two fluorine atoms have been removed and having the formula $C_{2n}F_{4n-2}$. When the production of compounds having the general formula $(R_fO)_xAr$ is desired ($R_f=C_{2n}F_{4n-1}$ and x=1 or 2) the temperatures should be maintained below 100° C., preferably in the range 10° C. to 80° C., the range of temperatures especially preferred being 20° C. to 55° C.

The reaction will take place at atmospheric pressure and thus for convenience this pressure is generally employed but a higher or lower pressure may be used if desired.

The proportions of the reactants used for the lower temperature reaction to make a compound having formula $R_fOAr$ are preferably substantially molar equivalents but clearly if compounds having the formula $R_f(OAr)_2$ are desired, two molar equivalents of the phenolic hydroxy compound are required to one of the oligomer. Moreover, if the reaction is carried out in the presence of a proton acceptor, substantially two molar equivalents of the proton acceptor should be used to activate the phenolic hydroxyl groups. Similarly in the case where the phenolic hydroxy compound is a dihydroxy compound (for example resorcinol) which clearly is capable of reacting with two molecules of oligomer to form a compound having the general formula $(R_fO)_2Ar$ substantially two molar equivalents of the oligomer will be required to satisfy one molar equivalent of the dihydroxy phenolic compound and, when the reaction is carried out in the presence of a proton acceptor, two molecules of the proton acceptor should be used. Although the reaction may be carried out using proportions of reactants very different from the stoichiometric, we prefer to use substantially stoichiometric proportions since these proportions generally give the best yields of the desired products.

The phenolic hydroxy compound may be used in the form of an alkali metal derivative (for example ArOM where M represents an alkali metal) or may be used in the presence of a proton acceptor. The alkali metal derivatives are not always convenient to prepare and consequently we generally prefer to use the phenolic hydroxy compound in the presence of a proton acceptor, for example an amine. Moreover, it is usually possible to obtain better yields by using the phenolic hydroxy compound in the presence of a suitable proton acceptor than by using an alkali metal derivative of the hydroxy compound.

When using an alcoholic hydroxy compound, we prefer that it be one in which the hydroxy of the hydroxyl group is readily replaceable by an alkali metal, for example aliphatic primary, secondary and tertiary alcohols, hydroxyesters, and hydroxy or alkoxy derivatives of these compounds, for example glycols, polyols and polymerised glycols.

The alcoholic hydroxy compound which may contain one or more alcoholic hydroxyl groups, may be substituted with groups which will take no part in the reaction with the fluorocarbon but which will modify the surface-active properties of the oligomer derivative produced in a desired manner, for example carboxyl ester, sulphonyl ester, and dialkyl amino groups. These further substituted groups, provided they are inert to the reaction conditions, may be completely as desired and are well-known in the art.

Examples of these compounds are mono and polyhydric alkenols and alkanols containing, for example, up to 20 carbon atoms, such as methyl, ethyl, butyl and octyl alcohol, allyl alcohol, ethylene glycol and glycerol, hydroxy-ethers and hydroxy-esters, for example ethylene glycol, monomethyl ether, polyethylene glycol monomethyl ethers $HO(CH_2CH_2O)_nCH_3$, ethylene glycol monoacetate, β-hydroxymethyl propionate, ethyl glycollate, ethyl lactate, isethionic acid $HOCH_2CH_2SO_3H$ and its salts.

As discussed above, reaction of the organic hydroxy compound with the tetrafluoroethylene oligomers proceeds by attack of oxy-anions derived from the hydroxy compound on the oligomer and accordingly the alcoholic hydroxy compound can be used in the form of an alkali metal derivatives thereof or in the presence of a proton acceptor especially the proton acceptors discussed above. For example, the same derivative is obtained by reacting the pentamer $(C_2F_4)_5$ with an alcoholic hydroxy compound in the presence of a proton acceptor, for example triethylamine, as is obtained when the pentamer is reacted with the corresponding alkali metal alkoxide.

The reaction of the alcoholic hydroxy compound (or its derivative) with the oligomer may be carried out at a temperature of from about $-80°$ C. to $150°$ C., optionally in a suitable organic solvent such as the solvents mentioned above. The lower part of this temperature range, that is from above $-80°$ C. to $40°$ C., is preferred for reactions in which a metal alkyl, for example n-butyl lithium, is used while the middle and upper parts, that is about $10°$ C. to $150°$ C., are preferred when using less reactive reagents.

The oligomer derivative prepared as primary reaction products possess surface-active properties in their own right. This surface-activity arises largely from the characteristic low surface free-energy properties of the perfluorocarbon group but its precise nature will, as noted above, depend on the nature of the organic residue attached to the oligomer. The organic residue may be attached to the oligomer in the desired form, or may be converted into the desired form by further chemical reaction on the oligomer derivative. Thus, when the hydroxy compound used contains aromatic group, the aromatic group may be substituted with other functional groups, for example halogen groups and sulphonyl, phosphoryl and carboxyl ester groups. However, in practice we prefer, mainly for economic reasons, to use aromatic compounds which are either unsubstituted or have only one or two short alkyl, preferably methyl substituent, and to modify the aromatic group by known chemical reactions after formation of the oligomer derivative. For example, the aromatic group in the oligomer derivative may be sulphonated, chlorosulphonated, chloromethylated or nitrated using known reagents. Moreover, alkyl substituents (for example methyl substituents) in the aromatic group of an oligomer derivative may be halogenated or oxidized in order to produce compounds with halogen, sulphonyl or carboxyl groups attached.

Examples of compounds containing aromatic groups which may be produced directly or indirectly in accordance with the present invention are:

$R_fOC_6H_5$ may be converted into:
 (a) $R_fOC_6H_4SO_2Cl$ by chlorosulphonation.
 (b) $R_fOC_6H_4SO_3H$ by sulphonation or by hydrolysis of the sulphonyl chloride obtained as above.
 (c) $R_fOC_6H_4Br$ by bromination.
 (d) $R_fOC_6H_4CH_2Cl$ by chloromethylation.

$R_fOC_6H_4CH_3$ may be converted into:
 (a) $R_fOC_6H_3(CH_3)SO_2Cl$ by chlorosulphonation.
 (b) $R_fOC_6H_4CH_2Cl$ by side-chain chlorination.
 (c) $R_fOC_6H_4CH_2Br$ by side-chain bromination.

$R_fOC_{10}H_7$ may be converted into:
 (a) $R_fOC_{10}H_6SO_2Cl$ by chlorosulphonation.
 (b) $R_fOC_{10}H_6SO_3H$ by sulphonation.
 (c) $R_fOC_{10}H_6Br$ by bromination.
 (d) $R_fOC_{10}H_6CH_2Cl$ by chloromethylation.

$(R_f)_2C_6H_4$ may be converted into:
 (a) $(R_fO)_2C_6H_3SO_2Cl$ by chlorosulphonation.
 (b) $(R_fO)_2C_6H_3SO_3H$ by sulphonation.

$R_f(OC_6H_5)_2$ may be converted into:
 (a) $R_f(OC_6H_4SO_2Cl)$ by chlorosulphonation.
 (b) $R_f(OC_6H_4NO_2)_2$ by nitration.
 (c) $R_f(OC_6H_4NH_2)_2$ by reduction.

$R_fOC_6H_4COOCH_3$ amy be converted into:
 (a) $R_fOC_6H_4COOH$ by acid hydrolysis.
 (b) $R_fOC_6H_4COCl$ by treatment of the corresponding carboxylic acid with a phosphorus chloride or thionyl chloride.
 (c) $R_fOC_6H_4CONH_2$ by treatment of the corresponding acid chloride with ammonia.
 (d) $R_fOC_6H_4CON(CH_3)_2$ by treatment of the corresponding acid chloride with dimethylamine.

Whilst the compounds described above are all derived from phenolic hydroxy compounds, it is to be understood that aromatic nuclei in compounds derived from alcoholic hydroxy compounds may equally be substituted in the aromatic group either before or after formation of the derivative.

Groups other than aromatic groups in the organic residue of the oligomer derivative may similarly be substituted and, again, the substituent may be present in the organic hydroxy compound used (provided the group concerned does not prevent the formation of the oligomer derivative) or may be inserted after formation of the oligomer derivative. When it is proposed to insert substitutes in the organic group after formation of the oligomer derivative we prefer to use an organic hydroxy compound having a suitable reactive site or functional group, for example an ester group as in for example ethylene glycol mono-acetate ($HOCH_2CH_2OOCCH_3$).

Optionally these reactive sites or functional groups may be converted to other desired groups after formation of the oligomer derivative; for example ester groups may be hydrolysed to the free acids and esters may be prepared from acids and alcohols using appropriate reagents (for example, an acid group may be reacted with acetylene or vinyl acetate to give a vinyl ester, and an alcohol may be reacted with acrylic or methacrylic acid to give an acrylate or methacrylate). Again, the organic residue may contain a chemically-linkable group, for example a polymerisable group, for example an isocyanate example a vinyl ester, acrylate or methacrylate group, introduced before or after formation of the oligomer derivative) so that polymers containing the oligomer derivative may be prepared. Such polymers exhibit oleophobic properties when applied to surfaces such as leather, textiles and paper.

As noted above, oligomer derivatives in accordance with the invention in which the organic residues are or contain hydrophilic groups exhibit remarkable surface-activity in aqueous solution. Especially useful are the derivatives of glycols and polyglcyols, for example polyethylene glycol monomethylethers, $HO(CH_2CH_2O)_nCH_3$ where n is an integer from 2 to 40. Examples of these derivatives are the novel anionic surface-active agents having the formulae:

$C_{10}F_{19}OC_6H_4CH_2O(CH_2CH_2O)_{22}$
$CH_2C_6H_4OC_{10}F_{19}$ $C_{10}F_{19}OC_6H_4CH_2O(CH_2CH_2O)_{33}CH_3$

Examples of other useful hydrophilic surfactants are oligomer derivatives of sulphonic acid, for example compounds prepared by reacting an oligomer with isethionic acid $HOCH_2CH_2SO_3H$ or the sodium salt thereof.

The invention is illustrated but not limited by the following Examples:

EXAMPLE 1

Sodium (1.1 g) was added in small portions to ethanol (60 ml) until formation of the ethoxide was complete. Tetrafluoroethylene pentamer (25 g) was then added dropwise to the stirred solution of sodium ethoxide in ethanol. An exothermic reaction took place during which sodium fluoride was precipitated. The whole reaction mixture was then distilled to remove excess ethanol. No unreacted pentamer remained and the residue after removal of all ethanol was distilled under vacuum to give 18 g of a viscous liquid, boiling point 72° C. to 76° C. at 2 mm Hg whose infra-red spectrum and quantitative analysis were consistent with that of the perfluoroalkenyl ethyl ether $C_{10}F_{19}OC_2H_5$. The product showed surface-active properties.

EXAMPLE 2

Sodio-diethyl malonate (prepared from sodium ethoxide (3.4 g) and diethyl malonate (8.0 g)) in dioxan (50 ml) and dimethyl formamide (50 ml) was heated and stirred under reflux with tetrafluoroethylene pentamer (25 g). After six hours the reaction mixture was cooled and filtered giving 2.2 g of sodium fluoride. The filtrate was poured into excess water and the lower layer separated. This layer was washed with water, dried and distilled to give 20 g of viscous liquid, boiling point 90° C. to 110° C. at 12 mm Hg.

The infra-red spectrum and elemental analyses of the product was consistent with that of the diethylperfluoroalkenyl malonate $C_{10}F_{19}CH(COOEt)_2$, and the product shows surface-active properties.

EXAMPLE 3

Sodium hydroxide (4 g) in excess ethylene glycol (25ml) was heated under vacuum to remove water.

To the resulting solution of mono-sodium ethylene glycollate in ethylene glycol was added tetrafluoroethylene pentamer (60 g). The reaction mixture was heated under reflux with vigorous stirring for twelve hours, and was then poured into water. The lower layer was washed with water, and the azeotroped with benzene to remove water and unreacted pentamer. The viscous liquid resulting after removal of the benzene exhibited hydroxyl absorption at 3 microns in the infra-red, together with strong absorption at 8.0 to 9.0 microns attributable to carbon-fluoride bonds. The compound shows surface activity.

EXAMPLE 4

Tetrafluoroethylene pentamer (100 g) was added slowly to an ether suspension of sodium allyl alcoholate (12 g). The resulting reaction mixture was refluxed for one hour, and unchanged pentamer and ether were removed under vacuum. The remaining product was cautiously diluted with water, and the lower layer separated. Distillation gave the desired perfluoroalkenyl allyl ether, $C_{10}F_{19}OCH_2CH=CH_2$, boiling point 54° C. to 58° C. at 1 mm Hg and shows surface-activity.

EXAMPLE 5

To a solution of tetrafluoroethylene pentamer (50 g) and ethyl alcohol (10 g) in $CF_2Cl.CFCl_2$ (100 ml) was added triethylamine (10 g). The resulting solution was heated under reflux for six hours, then the solvent was removed. The resulting product was washed with water, and then azeotroped with benzene to remove water and any unchanged pentamer. Distillation of the benzene solution gave a product identical to that obtained in Example 1, with the same surface-active properties.

EXAMPLE 6

Tetrafluoroethylene pentamer (250 g) was added slowly to a stirred suspension of sodio-methoxypolyethylene glycollate (molecular weight about 350) (140 g) in diethyl ether (750 ml). After stirring under reflux for one hour, the solution was filtered free of sodium fluoride, and the ether removed. Excess pentamer (45 g) was removed by heating under vacuum to leave a viscous liquid (300 g). Elemental analyses showed the product to be approximately $C_{10}F_{19}O(CH_2CH_2O)_7CH_3$. Aqueous solutions of the product showed marked surface activity as follows:

| Concentration wt. % | Surface tension dyn/cm |
|---|---|
| 0.1 | 20 |
| 0.01 | 24 |
| 0.001 | 36 |

EXAMPLE 7

Tetrafluoroethylene pentamer (250 g) with a sodiomethoxypolyethylene glycollate of molecular weight about 550 (200 g) gave a non-ionic surfactant analysing approximately as $C_{10}F_{19}O(CH_2CH_2O)_{11}CH_3$. Surface tension of aqueous solutions were as follows:

| Concentration wt. % | Surface tension dyn/cm |
|---|---|
| 0.1 | 19 |
| 0.01 | 21 |
| 0.001 | 32 |

EXAMPLE 8

Tetrafluoroethylene tetramer (200 g) was reacted as in Example 6 with sodio-methoxypolyethylene glycollate of molecule weight about 350 (130 g) to give 240 g of a product analysing as $C_8F_{15}O(CH_2CH_2O)_7CH_3$, which shows surface-activity.

EXAMPLE 9

A mixture containing tetrafluoro ethylene tetramer (100 g), sodium isethionate (37 g), triethylamine (30 g) in dry dimethyl formamide (500 ml) was vibromixed at 40° C. for seven hours. The mixture was filtered and allowed to settle into two layers. The lower layer, containing unreacted tetramer (65 g) was run off. Concentration of the dimethyl formamide (75 ml) acidification (2 N HCl) and dilution with water (150 ml) precipitated the crude product. The crude acid was extracted into ether (150 ml), washed well with water (3×50 ml) and then neutralised (2 N NaOH). Evaporation of the aqueous extract followed by acetone extraction of the residue and subsequent evaporation of the acetone yielded the desired sodium salt as a colourless solid (26 g). Spectroscopic and analytical data are in agreement with the proposed structure $C_8F_{15}OCH_2CH_2SO_3Na$.

The surface tension of an 0.1% aqueous solution of the sulphonate was 30.9 dyn/cm and at 0.01% concentration the value was 53.4 dyn/cm.

EXAMPLE 10

Tetrafluoroethylene pentamer (250 g) was added slowly to a stirred suspension of sodio-methoxypolyethylene glycollate (molecular weight about 350) (140 g) in dry diethyl ether (750 ml). After stirring under reflux for three hours, the solution was filtered free of sodium fluoride and the other evaporated in vacuo. Excess pentamer (45 g) was removed by heating under high vacuum to leave a viscous liquid (300 g). Elemental analyses showed the product to be $C_{10}F_{19}O(CH_2CH_2O)_7CH_3$.

Several other methoxypolyethylene glycol ethers of pentamer and tetramer have been synthesised as above. Aqueous solutions of these compounds showed marked surface-activity. Representative surface tension value of these are given in Table 1 below:

Table 1

| Compound | S.T. in dynes/cm | | |
|---|---|---|---|
| | 0.10% | 0.01% | 0.001% |
| $C_8F_{15}O(CH_2CH_2O)_7CH_3$ | 19 | 20 | 30 |
| $C_{10}F_{19}O(CH_2CH_2O)_7CH_3$ | 20 | 24 | 36 |
| $C_{10}F_{19}O(CH_2CH_2O)_{11}CH_3$ | 19 | 21 | 32 |
| $C_{10}F_{19}O(CH_2CH_2O)_{13}CH_3$ | 26 | 27 | 34 |
| $C_{10}F_{19}O(CH_2CH_2O)_{17}CH_3$ | 31 | 32 | 41 |

EXAMPLE 11

Tetrafluoroethylene pentamer (110 g) was reacted as in Example 2 with di-sodio-polyethylene glycollate of molecular weight 1000 (100 g) to give 190 g of a wax consistent with the formula $C_{10}F_{19}O(CH_2CH_2O)_{22}C_{10}F_{19}$.

Surface tension of aqueous solutions were as follows:

| Concentration Wt. % | Surface tension dyn/cm |
|---|---|
| 0.1 | 24 |
| 0.01 | 34 |
| 0.001 | 40 |

The analogue $C_{10}F_{19}O(CH_2CH_2O)_{33}C_{10}F_{19}$, prepared in the same manner, had surface tension values 27 dyn/cm of an 0.1% aqueous solution and at 0.01% and 0.001% concentrations the values were 29 dyn/cm and 32 dyn/cm respectively.

EXAMPLE 12

Tetrafluoroethylene pentamer (100 g) was slowly added to a stirred suspension of the sodio derivative of 2-diethylamine ethanol (28 g) in dry ether (250 ml). After stirring under reflux for four hours, the solution was filtered and then evaporated in vacuo. Distillation of the residue yielded a colourless liquid (42 g) boiling point 82° C. to 88° C. at 3 mm Hg. Spectroscopic and analytical data were in agreement with the formula $C_{10}F_{19}OCH_2CH_2N(C_2H_5)_2$. Quaternisation of an ethereal solution of this tertiary amine with dimethyl sulphate yielded a surface-active compound.

The surface tension of aqueous solutions of the compound $C_{10}F_{19}OCH_2CH_2N^+(C_2H_5)_2CH_3\ ^-CH_3SO_4$ were as follows:

| Concentration wt. % | Surface tension dyn/cm |
|---|---|
| 0.1 | 23 |
| 0.01 | 34 |

EXAMPLE 13

Tetrafluoroethylene pentamer (50 g) was added dropwise to sodium phenoxide (10 g) stirred in dimethyl formamide (100 ml) at 60° C. After addition of the pentamer, the reaction mixture was stirred for one hour at 60° C. and was then subjected to vacuum. Unchanged pentamer (10 g) and dimethyl formamide (90 ml) were distilled out, and the residue was poured into water. The oil which separated was dissolved in ether, the ether layer washed with water, dried over magnesium sulphate, and distilled to give 35.0 g of the phenyl ether $C_{10}F_{19}OC_6H_5$, boiling point 50° C. to 52° C. at 2 mm Hg. Elementary analysis, infra-red spectra, mass spectrometry and nuclear magnetic resonance measurements confirmed the identity of the compound.

A small amount of higher boiling residue was distilled to give 2.2 g of $C_{10}F_{18}(OC_6H_5)_2$.

This reaction was repeated in acetonitrile, dimethyl sulphoxide and hexamethyl phosphoramide. In each solvent, the same product $C_{10}F_{19}OC_6H_5$, was isolated. All products show surface-active properties.

EXAMPLE 14

Tetrafluoroethylene pentamer (150 g) was added dropwise to a stirred suspension of disodium-p-hydroxy-benzenesulphonate (43 g) in dimethyl formamide (500 ml) at 70° C. After stirring for two hours at 70° C. the excess pentamer (50 g) and dimethyl formamide (460 ml) were removed under vacuum, leaving a solid residue. This residue was dissolved in the minimum amount of hot water, and saturated brine was then added to precipitate the sodium salt of the desired sulphonic acid. The precipitate was filtered off, dried, extracted with ethanol and the ethanol extract concentrated to give 80 g of $C_{10}F_{19}OC_6H_4SO_3Na$.

$C_{10}F_{19}OC_6H_4SO_3Na$ requires: % C, 28.4; H, 0.6; F, 53.4; S, 4.7. Found: % C, 28.6; H, 0.54; F, 55.0; S, 4.9. The surface tensions of aqueous solutions of the sulphonate were as follows:

| Concentration wt. % | Surface tension dyn/cm |
|---|---|
| 0.1 | 22 |
| 0.01 | 30 |

EXAMPLE 15

Tetrafluoroethylene tetramer (150 g) was reacted with disodium-p-hydroxybenzenesulphonate (46 g) in acetonitrile (400 ml) at 80° C. After stirring under reflux for three hours, to product was isolated as in Example 14 to give 65 g of $C_8F_{15}O.C_6H_4.SO_3Na$.

$C_8F_{15}O.C_6H_4.SO_3Na$ requires: % C, 29.2; H, 0.7; F, 49.4; S, 5.6 Found: % C, 29.1; H, 1.3; F, 47.6; S, 6.2.

The surface tensions of aqueous solutions were as follows:

| Concentration wt. % | Surface tension dyn/cm |
| --- | --- |
| 0.1 | 20 |
| 0.01 | 40 |

Here again the low surface tensions provide very efficient surfactants.

EXAMPLE 16

Tetrafluoroethylene hexamer (150 g) was reacted with disodium-p-hydroxybenzenesulphonate (38 g) in dimethyl formamide (500 ml) as in Example 14 to give 75 g of $C_{12}F_{23}OC_6H_4SO_3Na$. Efficient surfactants are produced due to the low surface tension of aqueous solutions which were:

| Concentration wt. % | Surface tension dyn/cm |
| --- | --- |
| 0.1 | 22 |
| 0.01 | 28 |
| 0.001 | 31 |

EXAMPLE 17

Tetrafluoroethylene pentamer (250 g) was added dropwise to a stirred suspension of sodium-p-hydroxymethylbenzoate (70 g) in dimethyl formamide (750 ml) at 60° C. After two hours, the solvent and excess pentamer were removed to leave a viscous liquid. The viscous liquid was washed with water, dried and distilled to give 130 g of the ester $C_{10}F_{19}OC_6H_4COOCH_3$, boiling point 130° C. to 132° C. at 5 mm Hg.

Found: % C, 33.8; H, 0.9; F, 56.2.
Required: % C, 34.2; H, 1.1; F, 57.0.

EXAMPLE 18

Hydrolysis of the ester from Example 17 with aqueous caustic soda gave the sodium salt of the acid. The free acid was liberated by addition of dilute sulphuric acid. The free acid, $C_{10}F_{19}OC_6H_4COOH$, was recrystallised from benzene, melting point 127° C. to 128° C.

The sodium and ammonium salts of this acid showed high surface-activity when dissolved in water.

EXAMPLE 19

Reaction of the acid from Example 18 with acetylene (or in interchange reaction with vinyl acetate) gave the vinyl ester of the acid, $C_{10}F_{19}O.C_6H_4.COOCH=CH_2$, boiling point 115° C. to 120° C. at 1.5 mm.

Polymerisation of this vinyl ester (for example with t-butyl perbenzoate at 120° C.) gave a solid polymer insoluble in the common organic solvents, but soluble in $CF_2Cl.CFCl_2$ benzene and toluene.

Films of the polymer showed good water- and oil-repellency, and these effects could be obtained on textiles and on leather by treatment with a solution of the polymer.

EXAMPLE 20

Tetrafluoroethylene pentamer (150 g) was reacted with the sodium salt of p-hydroxybenzylalcohol (30 g) in dimethyl formamide (250 ml). Isolation of the product as in Example 17 gave 60 g of $C_{10}F_{19}OC_6H_4C-H_2OH$, boiling point 115° C. to 120° C. at 1 mm.

Found: % C, 33.6; H, 1.5; F, 60.8. Required: % C, 33.8; H, 1.2; F, 60.0.

The compounds show surface-activity.

EXAMPLE 21

The alcohol from Example 20 was converted to an acrylate by refluxing with excess methyl acrylate in an ester-interchange reaction. The resulting acrylate, a viscous liquid, polymerised on heating with free-radical initiators to give a polymer which exhibited both water- and oil- repellent properties and cotton treated by soaking therewith and drying shows the same properties.

For example, the acrylate $C_{10}F_{19}OC_6H_4C-H_2OCOCH=CH_2$, (5 g) was dissolved in benzotrifluoride (20 ml) containing t-butylperbenzoate (0.05 g) and was heated at 100° C. for six hours. On pouring the resulting polymer solution into methanol, 4.0 g of polymer was precipitated.

EXAMPLE 22

Tetrafluoroethylene pentamer (50 g) was added dropwise to the potassium salt of p-cresol (15 g) stirred in dry dimethyl formamide (100 ml) at 30° C. After addition of the pentamer, the reaction mixture was stirred for 45 minutes at 60° C. The cooled reaction mixture was poured into water. The oil which separated out was dissolved in ether, the ether layer washed with water, dried over magnesium sulphate, and distilled to give 40 g of the p-cresyl ether, $C_{10}F_{19}OC_6H_4CH_3$, boiling point 110° C. to 114° C. at 10 mm Hg. Elementary analysis, infra-red spectra, mass spectrometry and nuclear magnetic resonance measurements confirmed the identity of the compound.

EXAMPLE 23

Tetrafluoroethylene tetramer (40 g) was added dropwise to the potassium salt of p-cresol (15 g) stirred in dry dimethyl formamide (100 ml) at 25° C. to 30° C. After addition of the tetramer, the reaction mixture was stirred at 35° C. to 40° C. for two hours. The cooled reaction mixture was poured into water, and worked up as above to give 33 g of the -cresyl ether, $C_8F_{15}OC_6H_4CH_3$, boiling point 104° C. to 106° C. at 12 mm Hg. Elementary analysis, infra-red spectra, mass spectrometry and nuclear magnetic resonance measurements confirmed the identity of the compound.

EXAMPLE 24

To a stirred mixture of tetrafluoroethylene pentamer (5000 g) and phenol (1100 g) in a dry methylformamide (5 liters) at 45° C. was added dry triethylamine (1200 g). The rate of addition was such that the temperature was maintained at 45° C. to 50° C. and when the addition was complete, the reaction was maintained at this temperature for a further four hours before being allowed to cool to room temperature. The lower layer which formed was separated and washed successively with dilute hydrochloric acid and cold water until unreacted phenol and triethylamine were removed. Approximately 5000 g of a pale yellow liquid remained which had infra-red, mass and nuclear resonance spectra identical to those of $C_{10}F_{19}OC_6H_5$ produced by the published reactions in B.P. 1,130,822.

EXAMPLE 25

To a stirred mixture of tetrafluoroethylene pentamer (125 g) and dry ether (100 ml) was slowly added a mixture of p-hydroxymethylbenzoate (30 g) and triethylamine (20 g) in ether (300 ml). The whole mixture was stirred under gentle relux for five hours after which about 200 ml of ether was distilled off. The remaining solution was washed with dilute hydrochloric acid and water before being dried over magnesium sulphate and distilled. There was recovered 23 g of unreacted pentamer, and a main fraction (boiling point 135° C. to 145° C./4 to 5 mm, 75 g) was collected. This was identified by its spectra as $C_{10}F_{19}OC_6H_4COOCH_3$.

EXAMPLE 26

To a stirred mixture of tetrafluoroethylene pentamer (100 g) and triethylamine (20 g) in dimethylformamide (200 ml) was added slowly at room temperature a solution of α-naphthol (29 g) in dimethylformamde (100 ml). The mixture was stirred for two hours at room temperature then three hours at 50° C. before being cooled and poured into water. A lower layer was separated, washed with dilute hydrochloric acid, diluted with ether, the ether solution was then washed with water and dried over magnesium sulphate. Fractionation afforded a fraction (171° C. to 178° C./20 mm, 76 g) which solidified on cooling. It was recrystallised from isopropanol (melting point 69° C.) and identified by its infra-red, mass and nuclear resonance spectra as $C_{10}F_{19}OC_{10}H_7$ with α-substitution of the naphthalene nucleus.

EXAMPLE 27

To a stirred mixture of tetrafluoroethylene pentamer (100 g) and triethylene (20 g) in dimethylformamide (200 ml) was added slowly at room temperature a solution of β-naphthol (29 g) in dimethylformamide (100 ml). The mixture was stirred at room temperature for two hours then four hours at 50° C. before being cooled and poured into water. A lower layer was separated, diluted with ether, washed with dilute hydrochloric acid and water, then dried over magnesium sulphate, filtered and fractionated. A main fraction (175°C.–185° C./20 mm, 83 g) was collected and identified by its infra-red, mass and nuclear resonance spectra as $C_{10}F_{19}OC_{10}H_7$ with β-substitution of the naphthalene nucleus.

EXAMPLE 28

Reaction of tetrafluoroethylene pentamer with resorcinol. Resorcinol (22 g, 0.20 m) in dimethylformamide (100 ml) was added dropwise to a stirred mixture of tetrafluoroethylene pentamer (210 g, 0.42 m), triethylamine (40.5 g, 0.4 m) in dimethylformamide (300 ml). After stirring for five hours at 25° C. the reaction mixture was poured into cold water. The oil which separated was dissolved in ether, washed with 2N hydrochloric acid (50 ml) then with water and finally dried over magnesium sulphate. Removal of the ether by vacuum distillation left a colourless oil which distilled to yield 205 g of the resorcinyl ether of tetrafluoroethylene pentamer, boiling point 138° C.–140° C. at 1.4 mm Hg. Elemental analysis, infra-red spectra, mass spectrometry and nuclear magnetic resonance measurements were in complete agreement with the proposed structure $C_{10}F_{19}O(m\text{-}C_6H_4)OC_{10}F_{19}$.

EXAMPLE 29

Reaction of tetrafluoroethylene pentamer with phenol using N-ethyl piperidine as base. Phenol (10.3 g, 0.11 m) in dimethylformamide (70 ml) was added dropwise to a stirred mixture of tetrafluoroethylene pentamer (50 g, 0.10 m) and N-ethyl piperidine (12.4 g, 0.11 m) in dimethylformamide (70 ml). After stirring for three hours at 40° C. the lower layer was collected, washed well with water, dried over magnesium sulphate and distilled to yield 50.7 g of the phenyl ether $C_{10}F_{19}OC_6H_5$, boiling point 50° C.–52° C. at 2 mm Hg.

EXAMPLE 30

Reaction of tetrafluoroethylene pentamer with phenol using tri-n-butylamine as the base. Phenol (10.3 g, 0.11m) in dimethylformamide (70 ml) was added dropwise to a stirred mixture of tetrafluoroethylene pentamer (50 g, 0.10 m) tri-n-butylamine (20.3 g, 0.11 m) in dimethylformamide (70 ml). After stirring for three hours at 50° C. two layers separated on standing and the lower layer was collected, washed well with water and dried over magnesium sulphate. The dried product was distilled to yield 48 g of the phenyl ether $C_{10}F_{19}OC_6H_5$.

EXAMPLE 31

Dry triethylamine (252 g) was added slowly to a well mixed solution of p-cresol (270 g) and dry tetrafluoroethylene tetramer (1000 g) in dry dimethylformamide (2000 ml). The reaction temperature was kept below 35° C. by careful control of the addition of triethylamine. When addition of the reactants was complete, the reaction was conducted with stirring at ambient temperature for 20 hours. The products were poured into water, the lower layer separated off, washed first with diluted hydrochloric acid and then with water and finally dried over anhydrous magnesium sulphate. The dried product was filtered and distilled under reduced pressure to give the p-cresyl ether $C_8F_{15}OC_6H_4CH_3$, 1020 g, 84% yield, boiling point 96° C.–104° C./10 mm.

Found C, 37.2; H, 1.47%; Calc. for $C_{15}F_{15}H_7O$ C, 37.6; H, 1.44%.

Infra-red spectra, mass spectrometry and nuclear magnetic resonance measurements confirmed the identity of the compound.

EXAMPLE 32 p-Cresol (216 g) in dry dimethylformamide (200 ml) was added slowly to a well stirred mixture of dry tetrafluoroethylene pentamer (1000 g) and triethylamine (202 g) in dimethylformamide (300 ml). The reactants were left stirring at 40° C.–55° C. for 16 hours. The products were poured into water, the lower layer separated off, washed with dilute hydrochloric acid until all the amine was neutralised and the pH was below 7. Washing was continued with water and the product was dried over anhydrous magnesium sulphate. The dried product was filtered and distilled under reduced pressure to give the p-cresyl ether, $C_{10}F_{19}OC_6H_4CH_3$, 1080 g, 90% yield, boiling point 110° C.–112° C. at 10–12 mm Hg.

Infra-red spectra, mass spectrometry and nuclear resonance measurements confirmed the identity of the compound.

EXAMPLE 33

Dry triethylamine (102 g) was added slowly to a well mixed solution of phenol (94 g) and dry tetrafluoroethylene tetramer (400 g) in dry dimethylformamide (500 ml). The reaction temperature was kept below 30° C. by careful control of the addition of triethylamine. When addition was completed, the reactants were left stirring at ambient temperature for 16 hours. The products were poured into water, the lower layer separated off, washed with dilute hydrochloric acid and with water and finally dried over anhydrous magnesium sulphate. The dried product was filtered and distilled under reduced pressure to give the phenyl ether, $C_8F_{15}OC_6H_5$, 380 g, boiling point 60° C.–68° C./0.5 mm Hg.

Found: C, 34.9; H, 1.03%, Calc. for $C_{14}F_{15}H_5O$ C, 35.5; H, 1.05%.

Infra-red spectra, mass spectrometry and nuclear magnetic resonance measurements confirmed the identity of the compound.

EXAMPLE 34

Dry triethylamine (10.1 g) was added slowly to a well mixed solution of p-cresol (10.8 g) and dry tetrafluoroethylene hexamer (60 g) in dry dimethylformamide (120 ml). The reactants were left stirring at 50° C.–60° C. for seven hours. The products were poured into excess water, acidified with dilute hydrochloric acid and the lower layer separated off, The lower layer was washed with water, dried over anhydrous magnesium sulphate, filtered and distilled to give the p-cresyl ether: $C_{12}F_{23}OC_6H_4CH_3$, 53.5 g, 77% yield.

Boiling point 130° C.–135° C. at 10 mm Hg.

Infra-red spectra, mass spectrometry and nuclear magnetic resonance measurements confirmed the identity of the compound.

EXAMPLE 35

Dry triethylamine (50 g) was added slowly to a well mixed solution of phenol (47 g) and dry tetrafluoroethylene hexamer (300 g) in dry dimethylformamide (200 ml). The reactants were left stirring at 70° C.–80° C. for five hours. The products were poured into excess water, acidified with dilute hydrochloric acid and the lower layer separated off. The lower layer was washed with water, dried over anhydrous magnesium sulphate, filtered and distilled to give the phenyl ether: $C_{12}F_{23}OC_6H_5$, 210 g, 62% yield, boiling point 120° C.–125° C. at 10 mm Hg. Infra-red spectra, mass spectrometry and nuclear magnetic resonance measurements confirmed the identity of the compound.

EXAMPLE 36

Dry triethylamine (202 g) was added slowly to a well mixed solution of phenol (188 g) and dry tetrafluoroethylene pentamer (500 g) in dry dimethylformamide (500 ml). The reactants were left stirring at 80° C. for four hours. The products were poured into water, the lower layer separated off, washed with dilute hydrochloric acid, and then water, and finally dried over an anhydrous molecular sieve. The dried product was filtered and distilled under reduced pressure to give two compounds of the pentamer and phenol:

(1) The phenyl ether, $C_{10}F_{19}OC_6H_5$, 350 g, 61% yield, boiling point 100° C.–108° C. at 0.1 mm Hg and further distillation gave (2) The disubstituted phenyl ether: $C_{10}F_{18}(OC_6H_5)_2$, 65 g, 10% yield, boiling point 150° C.–160° C. at 0.1 mm Hg which was identified by infra-red spectra, mass spectrometry and nuclear magnetic resonance measurements.

EXAMPLE 37

The surface tensions of aqueous solutions of a variety of surface-active agents which have been made by the reactions shown diagrammatically in Examples 38–42 were measured. The results shown in Table 2 demonstrate that a considerable lowering of the surface tension of water is obtained even at very low concentrations of surface-active agent.

Table 2

| | Surface Tension Data in dynes/cm | | | | |
|---|---|---|---|---|---|
| | Concentration % | | | | |
| Compound | 1.0 | 0.1 | 0.01 | 0.001 | 0.0001 |
| $C_{10}F_{19}OC_6H_4NHCO(CH_2CH_2O)_{23}CH_3$ | — | 35 | 48 | 58 | 64 |
| $C_{10}F_{19}OC_6H_4CH_2O(CH_2CH_2)_{17}CH_3$ | 31 | 32 | 41 | — | — |
| $C_{10}F_{19}OC_6H_4CH_2PO_3Na_2$ | 24 | 25 | 40 | 50 | 62 |
| $C_{10}F_{19}OC_6H_4SO_2N(CH_3)CH_2CH_2SO_3Na$ | 23 | 25 | 29 | 36 | 46 |
| $C_{10}F_{19}OC_6H_4NHCH_2CH_2OSO_3Na$ | — | 42 | 60 | — | — |
| $C_{10}F_{19}OC_6H_4CH_2\overset{+}{N}(C_2H_5)_2(CH_2CH_2OH)Cl^-$ | 25 | 27 | 35 | 53 | 66 |
| $C_{10}F_{19}OC_6H_4CH_2\overset{+}{N}(C_2H_5)_3Cl^-$ | 25 | 28 | 40 | 55 | 64 |
| $C_{10}F_{19}OC_6H_4CH_2\overset{+}{N}(C_2H_5)_3I^-$ | 25 | 27 | 31 | 45 | 64 |

Further examples of the reactions of tetrafluoroethylene oligomer ethers are summarised in Schemes 1–5 wherein, $R_f$ is a branched perfluoroalkenyl group derived from tetrafluoroethylene preferably $C_8F_{15}$, $C_{10}F_{19}$ or $C_{12}F_{23}$.

R is hydrogen or an alkyl group preferably $C_1$-$C_6$ and especially methyl and ethyl.

M is a metal (or ammonium group) preferably an alkali metal and especially sodium or potassium.

n is an integer from 1 to 6.

m is an integer from 1 to 40.

X is Cl, Br, I.

Scheme 1

Examples of Reactions of Tetrafluoroethylene Oligomer Phenyl Ethers

Scheme 1
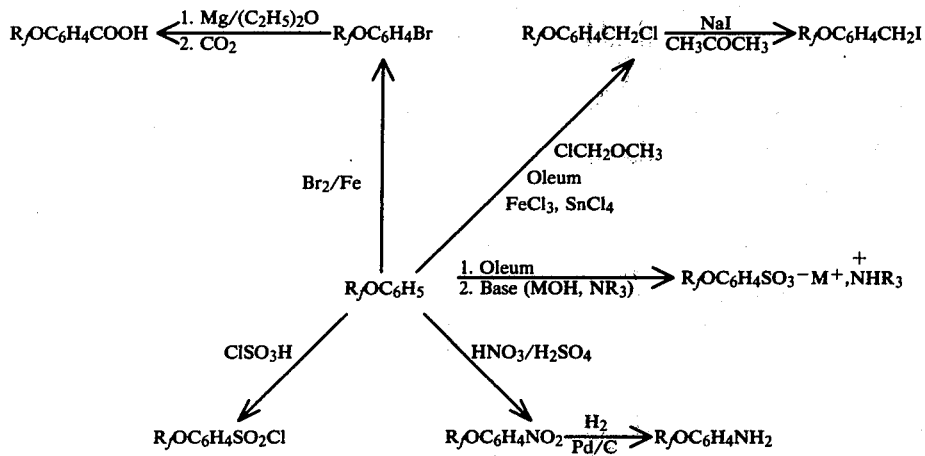
Scheme 2
Examples of Reactions of the p-Crosyl Ether of tetrafluoroethylene
Oligimers
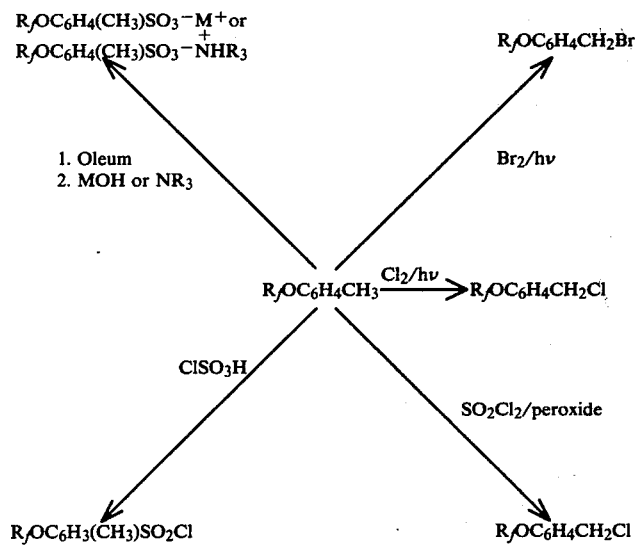
Scheme 3
Examples of the Conversion of p-Sulphonyl Cholride Phenyl
Ethers of Tetrafluoroethylene Oligomers into Compounds
for Industrial Application

Scheme 3

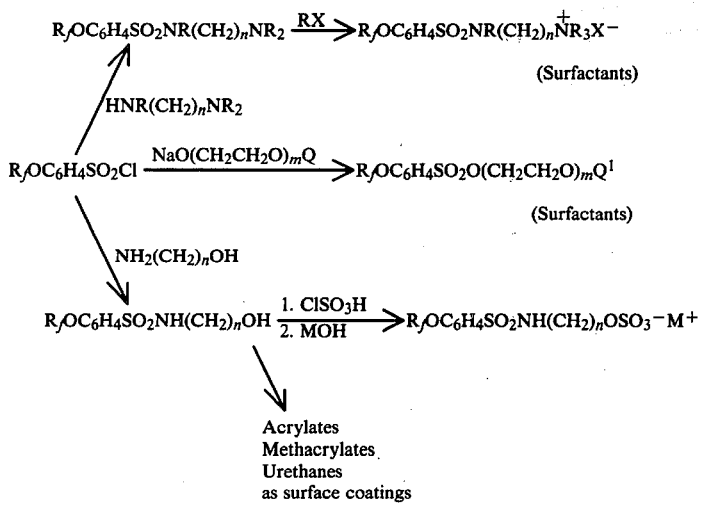

Key:
Either Q and $Q^1$ = alkyl or if Q = Na then Q = $SO_2C_6H_4OR_f$

Scheme 4

Examples of the Conversion of p-Benzyl Halide Ethers of
Tetrafluoroethylene Oligomers into Compounds for Industrial Application

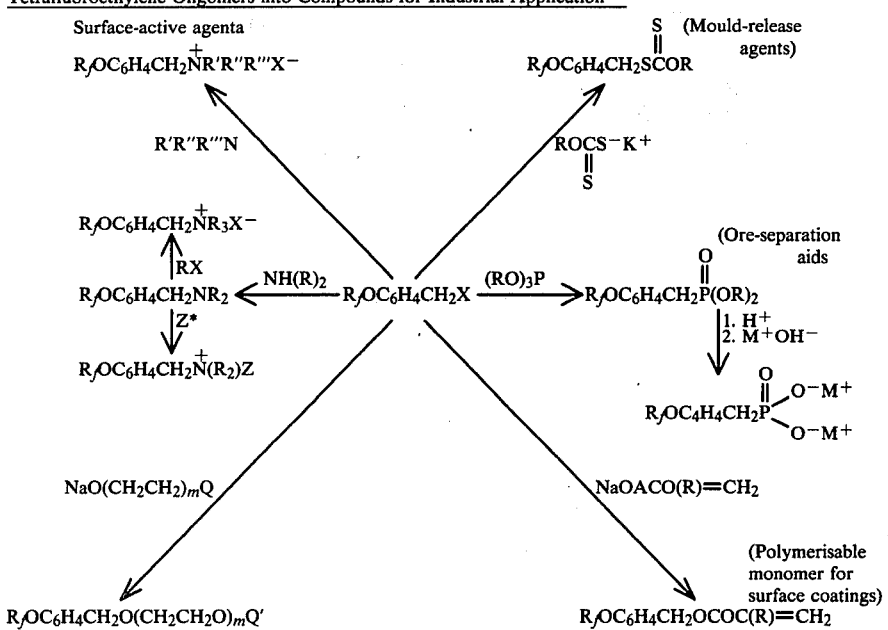

Key:
R' = H or alkyl; R''R''' = alkyl or pyridyl.
when Z* = $X(CH_2)_nCOOM$ then Z = $(CH_2)_nCOO^-$ when Z* = 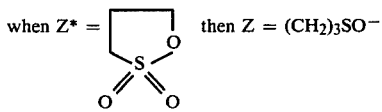 then Z = $(CH_2)_3SO^-$ when Z* = 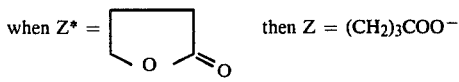 then Z = $(CH_2)_3COO^-$ when Q = alkyl then Q' = alkyl; when Q = Na then Q' = $R_fOC_6H_4CH_2$

Scheme 5
Examples of Conversion of the p-Amino Phenyl Ether of Tetrafluoroethylene Oligomers into Compounds for Industrial Application Surface coatings | Surfactants

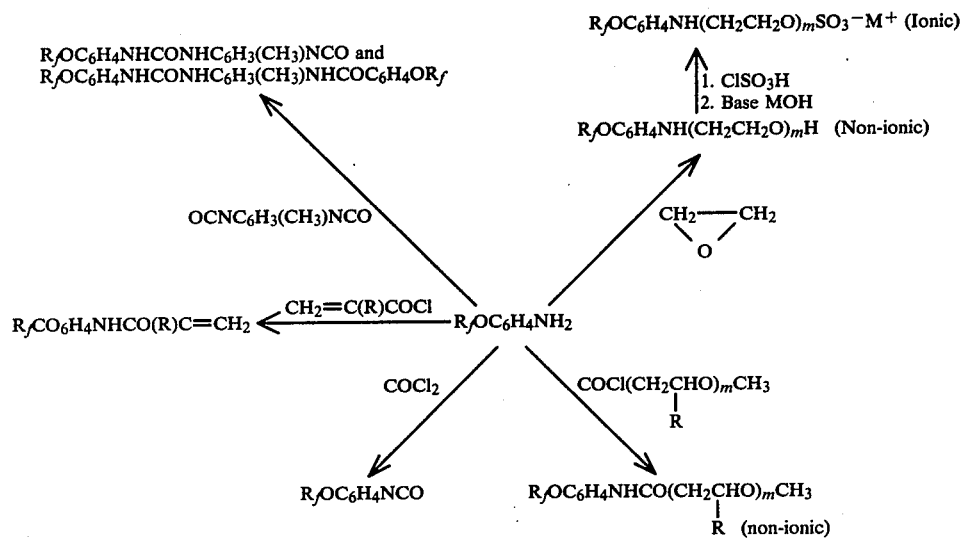

What we claim is:

1. A surface-active compound having a structure $R_f(OR)_x$ wherein $R_f$ is a radical $C_{2n}F_{4n-x}$ is which n is an integer equal to 4, 5 or 6 and x is an integer equal to 1 or 2 and said radical being a branched-chain, internally unsaturated perfluoroolefin which is a tetrafluoroethylene oligomer $C_{2n}F_{4n}$ minus x fluorine atoms, and wherein $R_f$ is attached by an ether linkage to another organic radical R, and ether linkage being through the hydroxyl group minus the hydrogen atom of the hydroxyl group, wherein the organic radical R contains a hydrophilic group and said hydrophilic group is selected from the group consisting of an oxyalkylene chain, a carboxylate salt or a sulphonate salt.

* * * * *